United States Patent [19]

White

[11] Patent Number: 5,537,881
[45] Date of Patent: Jul. 23, 1996

[54] FLUID SAMPLING DEVICE

[75] Inventor: Moreno J. White, Poway, Calif.

[73] Assignee: Sparta, Inc., San Diejo, Calif.

[21] Appl. No.: 490,806

[22] Filed: Jun. 16, 1995

[51] Int. Cl.⁶ ...................................................... G01N 1/12
[52] U.S. Cl. ........................................................ 73/864.63
[58] Field of Search .............. 73/864.63, 864.65–864.67

[56] References Cited

U.S. PATENT DOCUMENTS

| | | | |
|---|---|---|---|
| 2,059,629 | 11/1936 | Erwin et al. | 73/864.65 |
| 4,590,810 | 5/1986 | Hunkin et al. | 73/864.63 |
| 4,625,574 | 12/1986 | Robbins | 73/864.63 |
| 4,781,213 | 11/1988 | Kilayko . | |
| 4,883,505 | 11/1989 | Lucero | 73/863.21 |
| 5,341,692 | 8/1994 | Sher et al. | 73/864.63 |
| 5,442,970 | 8/1995 | Hutchins | 73/864.63 |

OTHER PUBLICATIONS

Article from *High–Performance Composites* Jul./Aug. 1994 edition, *Tape–Laying Precision Industrial Shafts* by Debbie Stover, pp. 29–32.

*Primary Examiner*—Robert Raevis
*Attorney, Agent, or Firm*—Stetina Brunda & Buyan

[57] ABSTRACT

A fluid sampling device has an elongate tube formed substantially of polyphenylene sulfide. A top end fitting is formed to the top end of the tube and is configured for connection to a tether. A bottom end fitting is similarly formed to the bottom end of the tube and has a check valve formed therein for allowing fluid to flow therethrough into the tube when the fluid sampling device is lowered into a fluid and for inhibiting fluid flow therethrough out of the tube when the tube is being raised and handled. The tube, top end fitting, bottom end fitting, and check valve are all formed of an inert material so as to maintain the integrity of the fluid sample collected. The use of polyphenylene sulfide provides a lightweight fluid sampling device which is durable enough to resist damage during routine handling and use.

18 Claims, 1 Drawing Sheet

U.S. Patent    Jul. 23, 1996    5,537,881
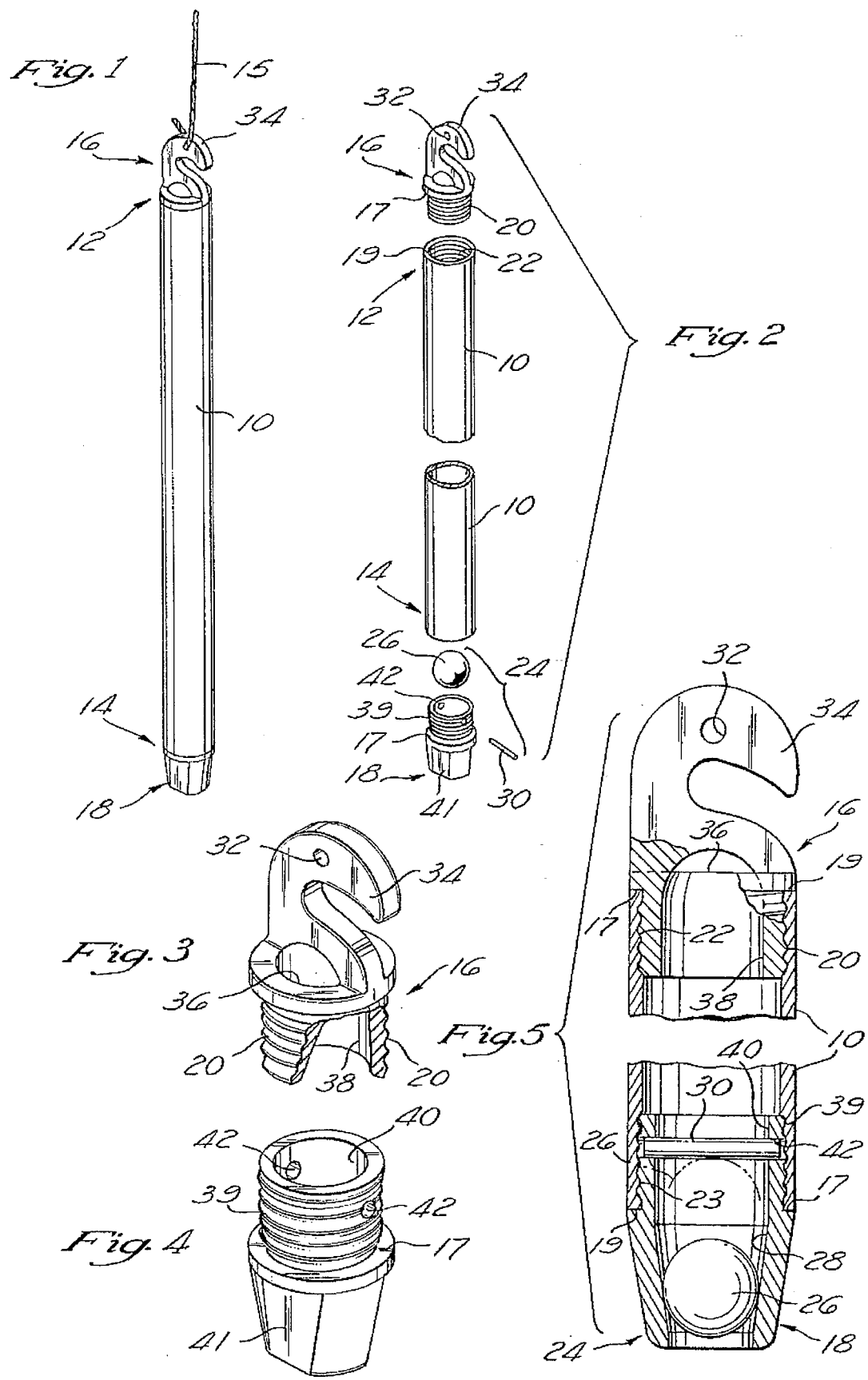

FLUID SAMPLING DEVICE

FIELD OF THE INVENTION

The present invention relates generally to sampling devices and more particularly to a fluid sampling device comprising an elongate tube formed of polyphenylene sulfide (PPS) having a top end fitting configured for connection to a tether and having a bottom end fitting which has a check valve formed therein. The tube, top end fitting, bottom end fitting, and check valve are all formed of substantially inert material so as to facilitate enhanced fluid sample integrity. Forming the tube substantially of polyphenylene sulfide substantially reduces the weight of the sampling device.

BACKGROUND OF THE INVENTION

Fluid sampling devices for the collection of fluid samples in wells, dump site drill holes, aquifer systems, and the like are well known. Such fluid sampling devices facilitate the analysis of collected fluid so as to determine the content of various contaminates and/or other specific constituents.

Two different types of prior art fluid sampling devices are currently utilized in such applications. The first of such prior art fluid sampling devices comprises a TEFLON (a registered trademark of Du Pont de Nemours, E. I., and Co., Inc.) tube with TEFLON/glass end fittings. The second utilizes a stainless steel tube with polymer or stainless steel end fittings.

The tube functions both as a collection device and as a container to hold the fluid sample after the sample has been collected and prior to pouring the sample fluid into a collection container.

A top end fitting serves as a pour spout to facilitate emptying of the device. An aperture is commonly formed in the top end fitting to facilitate the attachment of a drop line or tether which is used for lowering and raising the device.

Thus, contemporary fluid sampling devices are formed of comparatively inert materials, i.e., TEFLON, glass, stainless steel, or polymers, so as to reduce the likelihood of interaction between the materials of the fluid sampling device and the sampled fluid. It is desirable that the materials of the fluid sampling device neither add to nor modify the sample fluid constituents.

In this respect, TEFLON is more desirable than stainless steel. However, although TEFLON typically does not degrade due to environmental exposure, it is easily damaged by routine handling. Thus, although stainless steel is known to react with some of the constituents of the fluids to which it is exposed, stainless steel is frequently utilized in place of TEFLON because of its durability.

Additionally, stainless steel is considerably more heavy than TEFLON, thus further detracting from its desirability for such use. As those skilled in the art will appreciate, it is frequently necessary to hand carry such fluid sampling devices for substantial distances, particularly when sampling multiple sites within walking distance of one another.

As such, although the prior art has recognized to a limited extent the problem of obtaining fluid samples while maintaining the integrity thereof, the proposed solutions have, to date, been ineffective in providing a satisfactory remedy.

In view of the foregoing, it is clear that it would be beneficial to provide an improved fluid sampling device which is substantially inert to the sample constituents of the fluids to which it is exposed and which is light in weight, while also being durable enough to resist damage incurred from routine handling.

SUMMARY OF THE INVENTION

The present invention specifically addresses and alleviates the above-mentioned deficiencies associated with the prior art. More particularly, the present invention comprises a fluid sampling device comprising an elongate tube having top and bottom ends. The tube is comprised substantially of polyphenylene sulfide (PPS). A top end fitting formed or attached to the top end of the tube is configured for connection to a drop line or tether. The top end fitting is comprised of a substantially inert material, such as TEFLON, glass, polymer, or stainless steel.

A bottom end fitting is formed or attached to the bottom end of the tube. The bottom end fitting is likewise comprised of a substantially inert material, such as TEFLON, glass, polymer, or stainless steel.

A check valve is formed within the bottom end fitting. The check valve allows fluid flow therethrough into the tube and inhibits fluid flow therethrough out of the tube. The check valve is likewise comprised of a substantially inert material, such as TEFLON, glass, polymer, or stainless steel.

Forming the tube, the top end fitting, the bottom end fitting, and the check valve of such a substantially inert material, i.e., polyphenylene sulfide facilitates improved sample integrity by inhibiting chemical interactions between the materials of which the fluid sampling device is comprised and the constituents of the fluid sample. Thus, improved accuracy and reliability of the analysis of the fluid sample is facilitated.

Forming the tube substantially of polyphenylene sulfide substantially reduces the weight of the fluid sampling device while facilitating the fabrication of a device which is sufficiently durable to resist damage due to routine handling and use thereof.

The tube preferably comprises fiber reinforced polyphenylene sulfide. More particularly, the tube preferably comprises an extruded glass/polyphenylene sulfide inner tube and a carbon/polyphenylene sulfide tape outer layer.

According to the preferred embodiment of the present invention, an extruded inner tube of chopped glass reinforced polyphenylene sulfide is used as a mandrel upon which multi-layer carbon/polyphenylene sulfide tape is wrapped in an in-situ melt process such as that provided by Automated Dynamics Corp. of Schenectady, New York, and discussed in *High Performance Composites*, July/August, 1994, pp 29–32.

According to this process, carbon/polyphenylene sulfide tape is wrapped around a mandrel. The tape is then heated above its melting point, typically above approximately 590° F. A compaction roller then provides in-situ consolidation by applying pressure to the tape, generally in excess of 100 psi.

According to the preferred embodiment of the present invention, the tube is threaded at the top and bottom ends thereof and the top and bottom end fittings are threaded in a manner complimentary to the top and bottom ends of the tube so as to facilitate removable attachment thereto. Preferably, the threads formed at the top and bottom ends of the tube and the threads formed upon the top and bottom end fittings comprise rolled threads similar to those utilized on screw shells and lamp bases according to American Standand (Mogul 4TPI), so as to provide for easy attachment and removal of the top and bottom end fittings while maintaining an adequate fluid seal.

The top end fitting preferably comprises both an aperture or eyelet to which the drop line or tether is attachable and a hook which may be utilized to retrieve the fluid sampling device if the tether breaks. The top end fitting is also preferably configured to function as a pour spout.

The check valve preferably comprises a ball movably disposed within the bottom end fitting and a seat formed within the bottom end fitting upon which the ball rests so as to seal fluid within the tube. Thus, when the fluid sampling device is lowered through a fluid, viscous flow of the fluid through the bottom end fitting moves the ball away from the seat, thereby allowing fluid to flow into the tube. When the fluid sampling device is raised, viscous flow through the tube causes the ball to abut the seat, and the weight of the fluid maintains the ball against the seat, thereby inhibiting flow of the fluid through the bottom end fitting and check valve. Thus, the collected fluid is maintained within the tube while the tube is being raised.

A stop captures the ball within the bottom end fitting such that the ball is movable between a position abutting the seat wherein fluid flow is inhibited and a position spaced away from the seat wherein fluid flow is facilitated. The stop preferably comprises a rod which extends radially through the bottom end fitting so as to capture the ball within the bottom end fitting. Those skilled in the art will appreciate that various different types of stops, e.g., detents, spoons, bumps, protrusions, etc., are likewise suitable for limiting movement of the ball, as desired.

Additionally, those skilled in the art will appreciate that various different types of check valves, e.g., flap-type, pin and seat, etc., are likewise suitable for facilitating water flow into the tube through the bottom end fitting while preventing water flow out of the tube through the bottom end fitting.

These, as well as other advantages of the present invention will be more apparent from the following description and drawings. It is understood that changes in the specific structure shown and described may be made within the scope of the claims without departing from the spirit of the invention.

BRIEF DESCRIPTION OF THE DRAWINGS

FIG. 1 is a perspective view of the fluid sampling device of the present invention, having the top and bottom end fittings installed within the tube;

FIG. 2 is a fragmentary perspective view of the fluid sampling device of FIG. 1 showing the top and bottom end fittings exploded away from the tube and also showing the ball and rod of the check valve exploded away from the bottom end fitting;

FIG. 3 is an enlarged perspective view of the top end fitting showing the threads for attaching to the top end of the tube and also showing the eyelet and hook thereof;

FIG. 4 is an enlarged perspective view of the bottom end fitting showing the threads thereof; and FIG. 5 is a fragmentary cross-sectional side view of the fluid sampling device of the present invention, showing the ball and seat of the check valve.

DETAILED DESCRIPTION OF THE PREFERRED EMBODIMENT

The detailed description set forth below in connection with the appended drawings is intended as a description of the presently preferred embodiment of the invention, and is not intended to represent the only form in which the present invention may be constructed or utilized. The description sets forth the functions and sequence of steps for constructing and operating the invention in connection with the illustrated embodiment. It is to be understood, however, that the same or equivalent functions and sequences may be accomplished by different embodiments that are also intended to be encompassed within the spirit and scope of the invention.

The fluid sampling device of the present invention is illustrated in FIGS. 1–5 which depict a presently preferred embodiment of the invention. Referring now to FIGS. 1–5, the fluid sampling device generally comprises an elongate tube 10 having top end 12 and bottom end 14 thereof. A top end fitting 16 is attached to the top end 12 of the tube 10. Similarly, a bottom end fitting 18 is attached to the bottom end 14 of the tube 10.

With particular reference to FIG. 2, the top end fitting 16 preferably comprises threads 20 and the top end 12 of the tube 10 preferably comprises complimentary threads 22 so as to facilitate attachment of the top end fitting 16 to the top end 12 of the tube 10. Similarly, the bottom end fitting 18 preferably comprises threads 39 and the bottom end 14 of the tube 10 preferably comprises complimentary threads 23 (as shown in FIG. 5) so as to facilitate attachment of the bottom end fitting 18 to the bottom end 14 of the tube 10. The threads 20 of the top end fitting 16, the threads 22 of the top end 12 of the tube 10, the threads 39 of the bottom end fitting 18, and the threads 23 of the bottom end 14 of the tube 10 all preferably comprise rolled threads, preferably similar to those utilized in screw shells and lamp bases according to American Standard (Mogul 4TPI) so as to facilitate smooth and easy threading of the top fitting 16 and bottom fitting 18 to the tube 10, even in the presence of substantial particulate matter, e.g., soil, such as is common in water-sampling applications. Such threads have been found to provide adequate sealings of the tube, particularly in combination with the shoulder configuration of the top 16 and bottom 18 end fittings, as discussed in detail below.

With particular reference to FIG. 5, a check valve formed within the lower end fitting 18 preferably comprises a ball 26, a seat 28, and a stop or rod 30, as discussed in further detail below.

The top end fitting 16 preferably further comprises an eyelet 32 for attaching a drop line or tether to the fluid sampling device and a hook 34 which facilitates retrieval of the fluid sampling device in the event of a tether breakage, as described in further detail below. As used herein, the term tether is defined to include rope, cord, string, thread, wire, chain, and any other elongate flexible member, material, or device which is suitable for raising and lowering the fluid sampling device.

The top end fitting 16 is preferably configured so as to function as a pour spout by further comprising opening 36 through which the fluid contained within the tube 10 can be poured into a collection container. According to the preferred embodiment of the present invention, the opening 36 is formed upon both sides of the top end fitting 16. Those skilled in the art will appreciate that various other configurations are similarly suitable for facilitating use of the top end fitting 16 as a pour spout. A bore 38 is formed through the top end fitting 16 so as to provide fluid communication between the opening 36 and the interior of the tube 10.

The bottom end fitting 18 comprises a bore 40 formed therethrough so as to provide fluid communication through the bottom end fitting 18 into the interior of tube 10. The lowermost portion of the bore 40 is tapered so as to define seat 28. The rod 30 extends through apertures 42 formed in the bottom end fitting 18 so as to capture the ball 26 therein.

When fluid pressure on the lower surface of the ball 26 is greater than fluid pressure on the upper surface of the ball 26, as during lowering of the fluid sampling device through a fluid, the ball 26 moves to an uppermost position wherein it contacts the rod 30 so as to allow fluid to flow into the tube 10. Conversely, when fluid pressure upon the upper surface of the ball 26 is greater than fluid pressure upon the lower surface of the ball 26, as when the fluid sampling device is being raised, then the ball 26 abuts the seat 28, thereby sealing the bore 40 of the bottom end fitting 18 and thus trapping the sampled fluid within the interior of tube 10.

When the top end fitting 16 and the bottom end fitting 18 are completely threaded into the tube 10, the shoulder 17 of the top end fitting 16 and the shoulder 19 of the bottom end fitting 18 abut corresponding shoulders 17 of the tube 10, so as to provide adequate fluid seal to maintain the sample fluid within the tube 10. As those skilled in the art will appreciate, an O-ring or other sealing device may be utilized to further enhance such sealing.

As discussed above, the tube is comprised substantially of polyphenylene sulfide and the top and bottom end fittings and the check valve are comprised of a substantially inert material, such as TEFLON, glass, polymer, or stainless steel. The tube preferably comprises fiber reinforced polyphenylene sulfide, preferably an extruded glass/polyphenylene sulfide inner tube, and a carbon/polyphenylene sulfide tape outer layer, as discussed above.

Having described the structure of the present invention, it may be beneficial to discuss the operation thereof in detail. To use the fluid sampling device of the present invention, a drop line or tether is attached thereto, preferably via eyelet 32 formed in the top end fitting 16.

The fluid sampling device is then lowered into a well, dump site drill hole, aquifer system, or other fluid containing structure or vessel via the tether 15. As the fluid sampling device is lowered, fluid pressure builds up upon the lower surface of the ball 26, thereby urging the ball 26 into an upper most position wherein the ball 26 is disposed away from seat 28 and may contact rod 30. In this position, the check valve defined by ball 26, seat 28, and rod 30 facilitates fluid flow through the bottom end fitting 18 and into the interior of tube 10 such that a fluid sample is collected.

The fluid sampling device is then raised via the tether 15. Raising the fluid sampling device causes fluid pressure to increase upon the upper surface of the ball 26 such that the ball 26 is urged downwardly into abutment with the seat 28 in a manner which seals fluid within the interior of tube 10.

After the fluid sampling device has been withdrawn from the well, dump site drill hole, aquifer system, or other fluid containing structure or vessel, then the fluid sample may then be poured from the tube 10 via the pour spout defined by the openings 36 formed in the top end fitting 16.

In the event that the tether 15 breaks, slips from the user's hand, becomes untied, or the fluid sampling device otherwise is not retrievable from the well, dump site drill hole, aqua system, etc. via the tether 15, then an attempt may be made to retrieve the fluid sampling device by catching the hook 34 thereof with a hook or loop formed at the lower end of a second tether.

It is understood that the exemplary fluid sampling device described herein and shown in the drawings represents only a presently preferred embodiment of the invention. Indeed, various modifications and additions may be made to such embodiment without departing from the spirit and scope of the invention. For example, the tube 10 may be formed to have various cross sections other than the circular cross section illustrated. For example, the cross section of the tube 10 may alternatively be square, triangular, hexagonal, octagonal, etc. Additionally, various alternative configurations of the top and bottom end pieces are likewise contemplated.

Additionally, various alternative applications of the fluid sampling device of the present invention are contemplated. For example, the fluid sampling device may be utilized to sample fluids from fluid storage tanks such as those commonly utilized to store various petroleum products, mineral oil, vegetable oil, etc. Further, the fluid sampling device of the present invention may be utilized to collect samples from storm drains and sewers, as well as various natural bodies such as lakes, rivers, ponds, etc. Thus, these and other modifications and additions may be obvious to those skilled in the art and may be implemented to adapt the present invention for use in a variety of different applications.

What is claimed is:

1. A fluid sampling device comprising:
   a) an elongate tube having top and bottom ends, said tube comprised substantially of an extruded glass/polyphenylene sulfide inner tube and a carbon/polyphenylene sulfide tape outer layer;
   b) a top end fitting formed to the tope end of said tube and configured for attachment to a tether, said top end fitting comprised of a substantially inert material;
   c) a bottom end fitting formed to the bottom end of said tube, said bottom end fitting comprised of substantially inert material;
   d) a check valve formed within said bottom end fitting, said check valve allowing fluid flow therethrough into said tube and inhibiting fluid flow therethrough out of said tube, said check valve comprised of substantially inert material; and
   e) wherein forming said tube, said top end fitting, said bottom end fitting, and said check valve of substantially inert material facilitates improved fluid sample integrity and wherein forming said tube substantially of polyphenylene sulfide reduces the weight thereof.

2. The fluid sampling device as recited in claim 1 wherein said inner tube is comprised of chopped glass reinforced polyphenylene sulfide.

3. The fluid sampling device as recited in claim 2 wherein said chopped glass reinforced polyphenylene sulfide inner tube defines a mandrel about which multiple layers of carbon/polyphenylene sulfide tape are wrapped.

4. The fluid sampling device as recited in claim 1 wherein said top and bottom end fittings comprise at least one of Teflon/glass, polymer, and stainless steel.

5. The fluid sampling device as recited in claim 1 wherein:
   a) said tube comprises threads formed at the top and bottom ends thereof;
   b) said top end fitting comprises threads complimentary to those formed at the top end of said tube to facilitate attachment of said top end fitting to said tube; and
   c) said bottom end fitting comprises threads complimentary to those formed at the bottom end of said tube to facilitate attachment of said bottom end fitting to said tube.

6. The fluid sampling device as recited in claim 5 wherein said threads formed at the top and bottom ends of said tube and said threads formed upon said top and bottom end fittings, comprise rolled threads.

7. The fluid sampling device as recited in claim 1 wherein said top end fitting comprises at least one of an eyelet and a hook.

8. The fluid sampling device as recited in claim 1 wherein said top end fitting comprises both an eyelet and a hook.

9. The fluid sampling device as recited in claim 1 wherein said top end fitting is configured to function as a pour spout.

10. The fluid sampling device as recited in claim 1 wherein said check valve comprises:
   a) a ball movably disposed within said bottom end fitting;
   b) a valve seat formed within said bottom end fitting;
   c) a stop formed within said bottom end fitting so as to capture said ball therein; and
   d) wherein said ball moves away from said seat when said fluid sampling device is lowered to allow fluid to flow into said tube and said ball abuts said seat when said fluid sampling device is raised to inhibit fluid from flowing out of said tube.

11. The fluid sampling device as recited in claim 10 wherein said stop comprises a rod extending radially through said bottom end fitting.

12. A fluid sampling device formed by a process comprising the steps of:
   a) providing an elongate tube having top and bottom ends, said tube comprised substantially of an extruded glass/polyphenylene sulfide inner tube and a carbon/polyphenylene sulfide tape outer layer;
   b) forming a top end fitting to the tope end of said tube, said tope end fitting comprised of a substantially inert material;
   c) forming a bottom end fitting tot he bottom end of said tube, said bottom end fitting comprised of a substantially inert material; and
   d) forming a check valve within said bottom end fitting, said check valve allowing fluid flow therethrough into said tube and inhibiting fluid flow therethrough out of said tube, said check valve comprised of a substantially inert material.

13. A process for forming a fluid sampling device, said process comprising the steps of:
   a) providing an elongate tube having top and bottom ends, said tube comprised substantially of an extruded glass/polyphenylene sulfide inner tube and a carbon/polyphenylene sulfide tape outer layer;
   b) forming a top end fitting to the tope end of said tube, said top end fitting comprised of a substantially inert material;
   c) forming a bottom end fitting to the bottom end of said tube, said bottom end fitting comprised of a substantially inert material; and
   d) forming a check valve within said bottom end fitting, said check valve allowing fluid flow therethrough into said tube and inhibiting fluid flow therethrough out of said tube, said check valve comprised of a substantially inert material.

14. The process as recited in claim 13 wherein said inner tube is comprised of chopped glass reinforced polyphenylene sulfide.

15. The process as recited in claim 14 wherein said chopped glass reinforced polyphenylene sulfide inner tube defines a mandrel about which multiple layers of carbon/polyphenylene sulfide tape are wrapped.

16. The process as recited in claim 13 wherein the step of providing an elongate tube comprised substantially of polyphenylene sulfide comprises the steps of:
   a) wrapping carbon/polyphenylene sulfide tape about an extruded glass/polyphenylene sulfide inner tube;
   b) heating the tape to a temperature above its melting point; and
   c) applying pressure to the tape to provide in-situ consolidation.

17. The process as recited in claim 16 wherein the tape is heated to a temperature above approximately 590° F.

18. The process as recited in claim 16 wherein the pressure applied to the tape is generally in excess of approximately 100 psi.

* * * * *